United States Patent
Prince et al.

(10) Patent No.: US 12,426,779 B2
(45) Date of Patent: Sep. 30, 2025

(54) SEGMENTING RETINAL OCT IMAGES WITH INTER-B-SCAN AND LONGITUDINAL INFORMATION

(71) Applicant: THE JOHNS HOPKINS UNIVERSITY, Baltimore, MD (US)

(72) Inventors: Jerry L. Prince, Timonium, MD (US); Aaron Carass, Towson, MD (US); Yufan He, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 438 days.

(21) Appl. No.: 17/996,374

(22) PCT Filed: Apr. 2, 2021

(86) PCT No.: PCT/US2021/025605
§ 371 (c)(1),
(2) Date: Oct. 17, 2022

(87) PCT Pub. No.: WO2021/216269
PCT Pub. Date: Oct. 28, 2021

(65) Prior Publication Data
US 2023/0337907 A1 Oct. 26, 2023

Related U.S. Application Data

(60) Provisional application No. 63/013,407, filed on Apr. 21, 2020.

(51) Int. Cl.
*A61B 3/10* (2006.01)
*G06T 7/00* (2017.01)
(Continued)

(52) U.S. Cl.
CPC ............ *A61B 3/102* (2013.01); *G06T 7/0012* (2013.01); *G06T 7/174* (2017.01); *A61B 3/1225* (2013.01);
(Continued)

(58) Field of Classification Search
None
See application file for complete search history.

(56) References Cited

U.S. PATENT DOCUMENTS

2020/0037872 A1* 2/2020 Shiba ................. G01B 9/02044

FOREIGN PATENT DOCUMENTS

WO 2018209174 A2 11/2018

OTHER PUBLICATIONS

Kazak, A. (Authorized officer), International Search Report and Written Opinion in corresponding International Application No. PCT/US2021/025605 mailed on Jun. 17, 2021, 7 pages.
(Continued)

*Primary Examiner* — Lennin R Rodriguezgonzalez
(74) *Attorney, Agent, or Firm* — MH2 Technology Law Group LLP

(57) ABSTRACT

Techniques for retinal layer segmentation are presented. The techniques include obtaining current optical coherence tomography (OCT) data for a retina; generating an estimated current en face image based on the current OCT data and an estimated current retinal layer segmentation; determining a registered previous retinal layer segmentation based on a previous retinal layer segmentation, a previous en face image, the estimated current en face image, and the estimated current retinal layer segmentation; updating the estimated current retinal layer segmentation using a deep neural network and based on the current OCT data and the registered previous retinal layer segmentation; repeating the generating, the determining, and the updating to obtain a
(Continued)

current retinal layer segmentation as the estimated current retinal layer segmentation; and outputting a property of the retina determined at least in part from the current retinal layer segmentation.

20 Claims, 6 Drawing Sheets

(51) Int. Cl.
*G06T 7/174* (2017.01)
*A61B 3/12* (2006.01)
(52) U.S. Cl.
CPC .............. *G06T 2207/10101* (2013.01); *G06T 2207/20084* (2013.01); *G06T 2207/30041* (2013.01)

(56) References Cited

OTHER PUBLICATIONS

Bhaduri, B. et al., "Ratiometric analysis of in vivo retinal layer thicknesses in multiple sclerosis". J. Biomed. Opt. 2016, 21(9), 095001.
Ngo, L. et al., "Deep Neural Network Regression for Automated Retinal Layer Segmentation in Optical Coherence Tomography Images". IEEE Transactions on Image Processing (vol. 29); 2019; 303-312.
Kugelman, J. et al., "Automatic segmentation of OCT retinal boundaries using recurrent neural networks and graph search". Biomedical Optics Express Nov. 1, 2018, vol. 9, No. 11, 5759-5777.
Bhaduri, Basanta et al. "Ratiometric analysis of in vivo retinal layer thicknesses in multiple sclerosis." Journal of biomedical optics 21.9 (2016): 095001-095001.
Chen, Jianxu et al. "Combining fully convolutional and recurrent neural networks for 3d biomedical image segmentation." Advances in neural information processing systems 29 (2016).
Fang, Leyuan et al. "Automatic segmentation of nine retinal layer boundaries in OCT images of non-exudative AMD patients using deep learning and graph search." Biomedical optics express 8.5 (2017): 2732-2744.
Gao, Yang et al. "Fully convolutional structured LSTM networks for joint 4D medical image segmentation." 2018 IEEE 15th international symposium on biomedical imaging (ISBI 2018). IEEE, 2018.
He, Yufan et al. "Fully convolutional boundary regression for retina OCT segmentation." Medical Image Computing and Computer Assisted Intervention—MICCAI 2019: 22nd International Conference, Shenzhen, China, Oct. 13-17, 2019, Proceedings, Part I 22. Springer International Publishing, 2019.

He, Yufan et al. "Towards topological correct segmentation of macular OCT from cascaded FCNs." Fetal, Infant and Ophthalmic Medical Image Analysis: International Workshop, FIFI 2017, and 4th International Workshop, OMIA 2017, Held in Conjunction with MICCAI 2017, Quebec City, QC, Canada, Sep. 14, Proceedings 4. Springer International Publishing, 2017.
He, Yufan et al. "Topology guaranteed segmentation of the human retina from OCT using convolutional neural networks." arXiv preprint arXiv:1803.05120 (2018).
Kugelman, Jason et al. "Automatic segmentation of OCT retinal boundaries using recurrent neural networks and graph search." Biomedical optics express 9.11 (2018): 5759-5777.
Lang, Andrew et al. "Intensity inhomogeneity correction of SD-OCT data using macular flatspace." Medical image analysis 43 (2018): 85-97.
Lang, Andrew et al. "Longitudinal graph-based segmentation of macular OCT using fundus alignment." Medical Imaging 2015: Image Processing. vol. 9413. SPIE, 2015.
Lang, Andrew et al. "Retinal layer segmentation of macular OCT images using boundary classification." Biomedical optics express 4.7 (2013): 1133-1152.
Milletari, Fausto et al. "V-net: Fully convolutional neural networks for volumetric medical image segmentation." 2016 fourth international conference on 3D vision (3DV). Ieee, 2016.
Ngo, Lua et al. "Deep neural network regression for automated retinal layer segmentation in optical coherence tomography images." IEEE transactions on image processing 29 (2019): 303-312.
Novikov, Alexey A. et al. "Deep sequential segmentation of organs in volumetric medical scans." IEEE transactions on medical imaging 38.5 (2018): 1207-1215.
Oguz, Ipek et al. "4D graph-based segmentation for reproducible and sensitive choroid quantification from longitudinal OCT scans." Investigative ophthalmology & visual science 57.9 (2016): OCT621-OCT630.
Ronneberger, Olaf et al. "U-net: Convolutional networks for biomedical image segmentation." Medical Image Computing and Computer-Assisted Intervention—MICCAI 2015: 18th International Conference, Munich, Germany, Oct. 5-9, 2015, Proceedings, Part III 18. Springer International Publishing, 2015.
Roy, Snehashis et al. "Temporal filtering of longitudinal brain magnetic resonance images for consistent segmentation." NeuroImage: Clinical 11 (2016): 264-275.
Saidha, Shiv et al. "Primary retinal pathology in multiple sclerosis as detected by optical coherence tomography." Brain 134.2 (2011): 518-533.
Tang, X. (Authorized officer), International Preliminary Report on Patentability issued in corresponding International Application No. PCT/US2021/025605 mailed on Oct. 25, 2022, 6 pages.

* cited by examiner

SEGMENTING RETINAL OCT IMAGES WITH INTER-B-SCAN AND LONGITUDINAL INFORMATION

CROSS-REFERENCE TO RELATED APPLICATIONS

This application is the national stage entry of International Patent Application No. PCT/US2021/025605, filed on Apr. 2, 2021, and published as WO 2021/216269 A1 on Oct. 28, 2021, which claims the benefit of U.S. Provisional Application No. 63/013,407, filed on Apr. 21, 2020, both of which are hereby incorporated by reference herein in their entireties.

GOVERNMENT SUPPORT

This invention was made with government support under grant EY024655 awarded by the National Institutes of Health. The government has certain rights in the invention.

FIELD

This disclosure relates generally to segmentation of Optical Coherence Tomography (OCT) retinal images.

BACKGROUND

In general, OCT is a non-invasive imaging modality that is widely used to scan the retina. An OCT scan obtains a plurality of images known as "B-scans". Each B-scan is a 2D image of a slice through the retina that is roughly perpendicular to the retina. Each B-scan is made up of a plurality of immediately adjacent 1D scans, known as "A-scans", which are generally perpendicular to the retina. The plurality of B-scans may be generally parallel (known as "rectangular" OCT scans), at regular angular intervals (known as "radial" OCT scans), or in concentric circles (known as "annular" OCT scans). Taken together, a series of adjacent B-scans define a 3D block referred to herein as an OCT "volume". Such a 3D block may be a rectangular prism (for rectangular OCT scans) or a cylinder (for radial and annular OCT scans). OCT volumes can provide 3D images of retinas, but such images omit data between B-scans.

Monitoring retinal thickness of persons with multiple sclerosis provides important bio-markers for disease progression. However, changes in retinal thickness can be small and concealed by noise in the acquired data.

Automated segmentation of OCT retinal volumes is difficult for many reasons. OCT-produced volumes are highly anisotropic. A typical standard-definition OCT B-scan resolution is 3.9×5.5 micron, but the distance between adjacent B-scans for rectangular OCT scans is about 118 microns. Naïve attempts to use interpolation between B-scans in a volume produce unreliable and inaccurate segmentation results. Likewise, segmentation techniques suitable for Magnetic Resonance Imaging (MRI) and Computed Tomography (CT) data are unsuitable for OCT due to the spacing between slices in the latter. Past attempts at retinal segmentation in OCT data using deep neural networks based on 2D B-scan images lack 3D inter-B-scan context. Directly applying 3D convolution networks with isotropic kernel to the anisotropic images of an OCT volume is inappropriate due to the inter-B-scan gaps.

SUMMARY

According to various embodiments, a method of retinal layer segmentation is provided. The method includes obtaining current optical coherence tomography (OCT) data for a retina; generating an estimated current en face image based on the current OCT data and an estimated current retinal layer segmentation; determining a registered previous retinal layer segmentation based on a previous retinal layer segmentation, a previous en face image, the estimated current en face image, and the estimated current retinal layer segmentation; updating the estimated current retinal layer segmentation using a deep neural network and based on the current OCT data and the registered previous retinal layer segmentation; repeating the generating, the determining, and the updating to obtain a current retinal layer segmentation as the estimated current retinal layer segmentation; and outputting a property of the retina determined at least in part from the current retinal layer segmentation.

Various optional features of the above embodiments include the following. The property of the retina may include a thickness of the retina. The property of the retina may include the current retinal layer segmentation. The determining the registered previous retinal layer segmentation may include: obtaining a transformation that registers the previous en face image to the estimated current en face image; applying the transformation to the previous retinal layer segmentation to align the previous retinal layer segmentation with the estimated current retinal layer segmentation in an en face plane, where a transformed previous retinal layer segmentation is obtained; and shifting the transformed previous retinal layer segmentation axially to align with a predetermined retinal layer, where the registered previous retinal layer segmentation is obtained. The repeating may include repeating until either a predetermined number of repetitions is completed or until the estimated current retinal layer segmentation converges. The method may include outputting a current three-dimensional retinal layer map. The current OCT data may include a plurality of two-dimensional images; the deep neural network may include a plurality of two-dimensional encoders and a plurality of convolutional long-short-term memory networks; and the updating the estimated current retinal layer segmentation using the deep neural network may include: extracting, using the plurality of two-dimensional encoders, intra-slice features from the two-dimensional scans, and extracting, using the plurality of convolutional long-short-term memory networks and based on the intra-slice features, inter-slice features from the two-dimensional scans. The deep neural network may include a plurality of convolutional networks; and where the updating the estimated current retinal layer segmentation using the deep neural network may include generating, by the plurality of convolutional networks, longitudinal priors for retinal layers based on at least the registered previous retinal layer segmentation. The method may include assessing a progression of multiple sclerosis based on the property of the retina. The current retinal layer segmentation may include at least three retinal layers.

According to various embodiments, a system for retinal layer segmentation is presented. The system includes at least one electronic processor and non-transitory computer readable instructions that configure the at least one processor to perform operations including: obtaining current optical coherence tomography (OCT) data for a retina; generating an estimated current en face image based on the current OCT data and an estimated current retinal layer segmentation; determining a registered previous retinal layer segmentation based on a previous retinal layer segmentation, a previous en face image, the estimated current en face image, and the estimated current retinal layer segmentation; updating the estimated current retinal layer segmentation using a deep neural network and based on the current OCT data and the registered previous retinal layer segmentation; repeating the generating, the determining, and the updating to obtain a current retinal layer segmentation as the estimated current retinal layer segmentation; and outputting a property of the retina determined at least in part from the current retinal layer segmentation.

Various optional features of the above embodiments include the following. The property of the retina may include a thickness of the retina. The property of the retina may include the current retinal layer segmentation. The determining the registered previous retinal layer segmentation may include: obtaining a transformation that registers the previous en face image to the estimated current en face image; applying the transformation to the previous retinal layer segmentation to align the previous retinal layer segmentation with the estimated current retinal layer segmentation in an en face plane, where a transformed previous retinal layer segmentation is obtained; and shifting the transformed previous retinal layer segmentation axially to align with a predetermined retinal layer, where the registered previous retinal layer segmentation is obtained. The repeating may include repeating until either a predetermined number of repetitions is completed or until the estimated current retinal layer segmentation converges. The operations further may include outputting a current three-dimensional retinal layer map. The current OCT data may include a plurality of two-dimensional images; the deep neural network may include a plurality of two-dimensional encoders and a plurality of convolutional long-short-term memory networks; and the updating the estimated current retinal layer segmentation using the deep neural network may include: extracting, using the plurality of two-dimensional encoders, intra-slice features from the two-dimensional scans; and extracting, using the plurality of convolutional long-short-term memory networks and based on the intra-slice features, inter-slice features from the two-dimensional scans. The deep neural network may include a plurality of convolutional networks; and the updating the estimated current retinal layer segmentation using the deep neural network may include generating, by the plurality of convolutional networks, longitudinal priors for retinal layers based on at least the registered previous retinal layer segmentation. The operations may further include assessing a progression of multiple sclerosis based on the property of the retina. The current retinal layer segmentation may include at least three retinal layers.

BRIEF DESCRIPTION OF THE DRAWINGS

Various features of the embodiments can be more fully appreciated, as the same become better understood with reference to the following detailed description of the embodiments when considered in connection with the accompanying figures, in which.

DESCRIPTION OF THE EMBODIMENTS

Reference will now be made in detail to example implementations, illustrated in the accompanying drawings. Wherever possible, the same reference numbers will be used throughout the drawings to refer to the same or like parts. In the following description, reference is made to the accompanying drawings that form a part thereof, and in which is shown by way of illustration specific exemplary embodiments in which the invention may be practiced. These embodiments are described in sufficient detail to enable those skilled in the art to practice the invention and it is to be understood that other embodiments may be utilized and that changes may be made without departing from the scope of the invention. The following description is, therefore, merely exemplary.

Accurate longitudinal (e.g., temporally sequential) retinal layer segmentation methods for OCT images would be useful for identifying the real longitudinal retinal changes of individuals with multiple sclerosis. Embodiments may be used to identify the boundaries, and thicknesses, of any, or any combination, of the following retinal layers: total retina, outer plexiform layer, outer nuclear layer, inner segment, outer segment, retinal pigment epithelium, ganglion cell, inner plexiform layer, ganglion cell with inner plexiform layer, retinal nerve fiber, and inner nuclear layer.

Some embodiments provide iterative registration and deep-learning-based segmentation for longitudinal (e.g., six to twelve month interval) 3D OCT retinal volumes. Because OCT volumes are anisotropic with large slice separation, some embodiments extract B-scan features using 2D deep networks and utilize inter-B-scan context with convolutional long-short-term memory networks. That is, to utilize 3D information (while avoiding 3D convolutions) some embodiments use a 2D network to extract intra-slice features and use convolutional long-short-term-memory networks to extract inter-slice features. To incorporate longitudinal information, e.g., information from a previous OCT scan, some embodiments perform en face registration and interpolate the smooth retinal layers of the previous visit to use as priors on the current visit. That is, some embodiments register the longitudinal retinal layers to a current OCT scan to provide longitudinal priors, e.g., Bayesian priors. Thus, such embodiments register the previous visit layer segmentation to OCT scan data for the current visit, and use the deep network to obtain the layer segmentation of the current visit.

Figure 1:
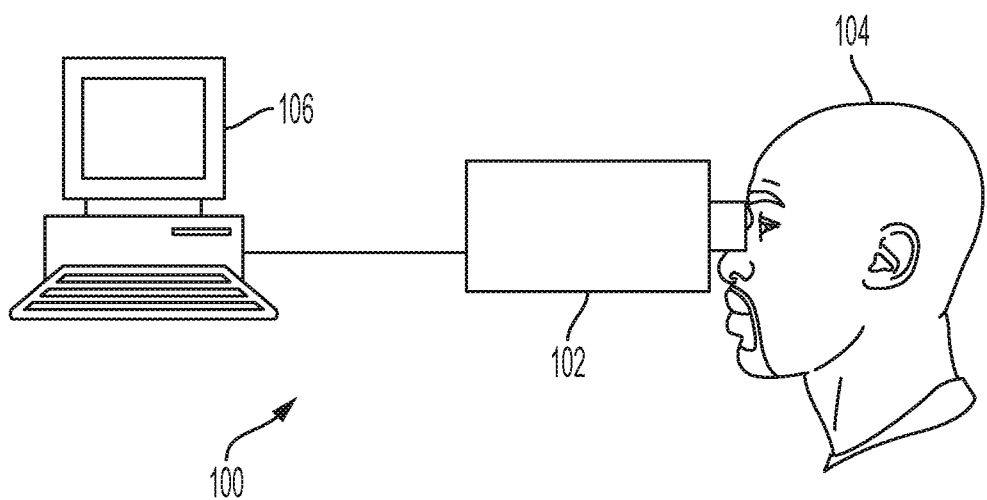
FIG. 1 is a schematic diagram of an OCT system according to various embodiments.

FIG. 1 is a schematic diagram of an OCT system 100 according to various embodiments. The system 100 includes OCT scanner 102, with which retina of patient 104 may be imaged. OCT scanner 102 is communicatively coupled to computer 106, which may perform image segmentation and image analysis as disclosed herein.

Retinal layer thickness changes within multiple sclerosis patients can be monitored by OCT volumes. Due to the diffusive and noisy retinal layer boundaries in the OCT volumes, segmentation based only on 2D B-scan images lacks the sensitivity for patient specific analysis. To achieve higher accuracy and consistent segmentation for monitoring disease progression, some embodiments utilize both context of adjacent B-scans (3D) and temporal longitudinal information (4D).

Figure 2:
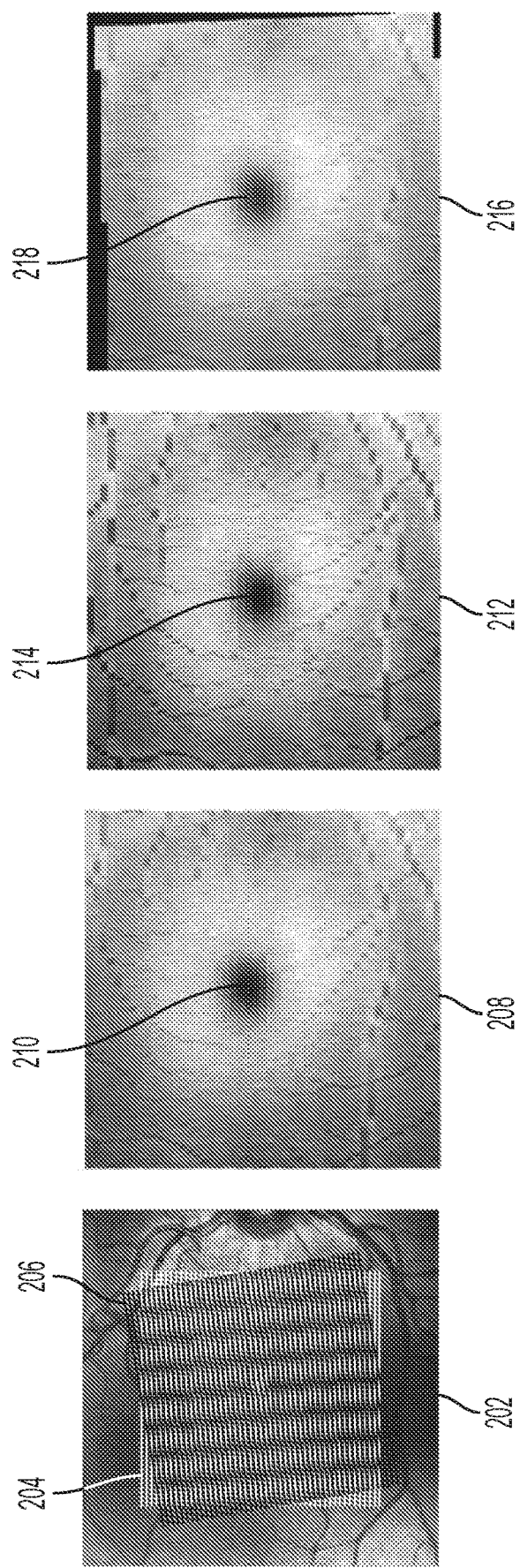
FIG. 2 depicts B-scan locations for two longitudinal rectangular OCT scans on an en face image of a retina, a generated en face image for a previous OCT scan, a generated en face image for a current OCT scan, and a transformed en face image according to various embodiments.

FIG. 2 depicts B-scan locations 204, 206 for two longitudinal rectangular OCT scans on an en face image 202 of a retina, a generated en face image 208 for a previous OCT scan including fovea 210, a generated en face image 212 for a current OCT scan including fovea 214, and a transformed en face image 216 including fovea 218 according to various embodiments As shown in FIG. 2, the B-scan locations 204, 206 illustrate that when the same patient is scanned twice longitudinally, there is still considerably slice separation. Such large slice separation makes direct interpolation between B-scans in a volume unreliable. Although direct interpolation of a spatial collection of B-scans produces inaccurate results, some embodiments interpolate the segmented smooth and continuous retinal surfaces across the whole retina.

Figure 3:
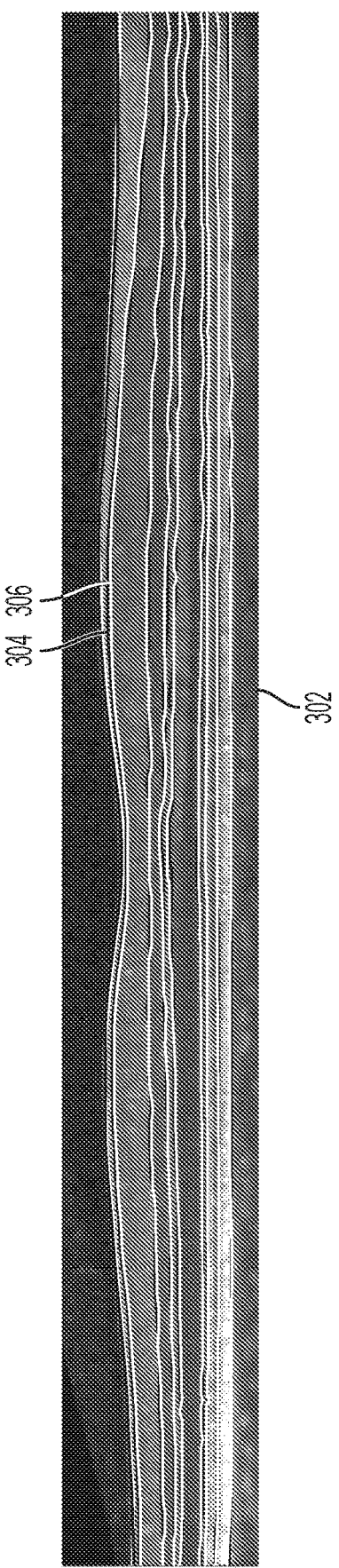
FIG. 3 depicts a flattened and cropped B-scan image of a retina overlaid with both a current retinal layer segmentation and a registered previous retinal layer segmentation according to various embodiments.

FIG. 3 depicts a flattened and cropped B-scan image 302 of a retina overlaid with both a current retinal layer segmentation 306 and a registered previous retinal layer segmentation 306 according to various embodiments. As a preprocessing step according to some embodiments, for each B-scan in a 3D retinal volume, the image is flattened to the estimated Bruch's membrane and cropped as depicted by flattened B-scan image 302.

Herein, the resulting volume of flattened B-scan images 302 for time t is denoted $x_t$ and its retinal layer segmentation for time t is denoted $s_t$. In practice, the volume $x_t$ may be implemented by an electronically stored 3D intensity matrix with indices [row number, column number, slice number], where each column is an A-scan and each slice is a B-scan. Thus, for example, $x_t[i,j,k]$ may represent the intensity of the i-th voxel of the j-th A-scan in the k-th B-scan in the volume. The retinal layer segmentation $s_t$ may be implemented as an electronically stored 3D matrix with indices [column number, slice number, surface number]. A continuous surface will intersect with each column at only one position. Thus, for example, $s_t[i,j,k]$ may represent that the k-th surface intersects with the i-th A-scan of the j-th B-scan at the $s_t[i,j,k]$-th voxel. Note that although $s_t$ may have units of voxels, it need not be an integer in general; when $s_t$ is not an integer, it indicates a surface position that lies between voxels. In general, as used herein, $x_t$ and $s_t$ may correspond to a current OCT scan, and $x_{t-1}$ and $s_{t-1}$ may correspond to a previous OCT scan.

Note that $x_t$ denotes a 3D volume composed of a spatial arrangement (e.g., a stack) of flattened and cropped 2D B-scan images, and $s_t$ may be characterized as a 3D matrix representing the depth position of each retinal layer at each A-scan in the B-scans of $x_t$. The retinal layer segmentation $s_t$ may identify the boundaries of any, or any combination, of the following retinal layers: total retina, outer plexiform layer, outer nuclear layer, inner segment, outer segment, retinal pigment epithelium, ganglion cell, inner plexiform layer, ganglion cell with inner plexiform layer, retinal nerve fiber, and inner nuclear layer.

Techniques disclosed herein are presented with respect to rectangular volumes for purposes of illustration rather than limitation; however, the disclosed techniques may be used for radial and annular OCT volumes as well.

Some embodiments utilize the following iterative Algorithm, e.g., implemented by computer 106 of FIG. 1, for retinal registration and segmentation, described in detail presently.

Algorithm: Iterative Registration and Segmentation (1) Input: $x_t$, $s_{t-1}$, $x_{t-1}$
(2) Initialize network Φ (see Fig. 4 and associated description) and define initial registered prior segmentation $s_{t-1}^r = 0$;
(3) Obtain en face image $f_{t-1}$ from ($s_{t-1}$, $x_{t-1}$) and initial current segmentation $s_t = \Phi(x_t, s_{t-1}^r)$;
(4) while iter < max_iter do
(5)  Obtain en face image $f_t$ from ($s_t$, $x_t$);
(6)  Obtain 2D affine transformation T by registering $f_{t-1}$ to $f_t$;
(7)  Transform $s_{t-1}$ with T to align $s_t$ in en face plane;
(8)  Obtain $s_{t-1}^r$ by shifting axially to align $s_t$ with IS-OS surface;
(9)  Update $s_t = \Phi(x_t, s_{t-1}^r)$;
(10) end while;
(11) Output: $s_t$ Some embodiments consider that the real anatomical retinal layer surface $r_{t-1}$ for an OCT scan at time t−1 (e.g., from a previous OCT scan) is close to the real current surface $r_t$. Surface segmentations $s_{t-1}$ and $s_t$ are digital samples of $r_{t-1}$ and $r_t$, respectively, at different sampling positions (e.g., B-scan locations 204, 206 of FIG. 2) so they can be very different unless registered.

Thus, some embodiments utilize the Algorithm as follows. At (1), the Algorithm accepts as input a current OCT volume $x_t$, a previous retinal layer segmentation $s_{t-1}$, and a previous OCT volume $x_{t-1}$. At (2), the Algorithm initializes a neural network Φ (e.g., as described in detail below in reference to FIG. 4) and sets an initial registered previous retinal layer segmentation $s_{t-1}^r$ corresponding to the previous volume to zero. Next, at (3), The Algorithm obtains a previous en face image, denoted $f_{t-1}$, from the previous segmentation and the previous volume, $s_{t-1}$, $x_{t-1}$, respectively, and determines a coarse estimated current retinal layer segmentation $s_t$ by applying Φ to the current OCT volume $x_t$ and the initial registered previous retinal layer segmentation $s_{t-1}^r$.

An iteration loop commences at (4).

At (5), The Algorithm generates en face images $f_{t-1}$ (e.g., 208 FIG. 2) and $f_t$ (e.g., 212 of FIG. 2) by intensity normalizing $x_t$ and $x_{t-1}$, respectively, summing up the intensities and total retina thicknesses from $s_t$ and $s_{t-1}$, and identifying and aligning the foveas (e.g., 210, 214), and then generates at (6) an affine transformation T from $f_{t-1}$ to $f_t$.

For purposes of illustration, a transformed en face image 216 generated by registering the previous en face image 208 to the current en face image 212 and then applying the corresponding registration transformation T to the previous en face image 208 is depicted in FIG. 2. That is, the transformed en face image 216 is generated by applying T to $f_{t-1}$ 214.

Actions (7) and (8) provide registration of the previous retinal layer segmentation to the current OCT data. Thus, at (7), the Algorithm applies T to $s_{t-1}$ to align $s_t$ in the en face plane. At (8), the Algorithm aligns the transformed surfaces $T(s_{t-1})$ and $s_t$ in the axial (e.g., A-scan) direction by shifting axially to align a selected retinal layer, such as the junction between the retinal photoreceptor's inner and outer segments (IS-OS), the seventh retinal surface from the top. Through en face registration (7) and layer alignment (8), embodiments determine a registered previous retinal layer segmentation, denoted herein as $s_{t-1}^r$ which is close to $s_t$.

A B-scan from $x_t$ with a 2D slice from the registered previous retinal layer segmentation $s_{t-1}^r$ overlaid is depicted in FIG. 3 by image 302. As shown, registered previous retinal layer segmentation $s_{t-1}^r$ 306 provides a good prior for the estimated current segmentation $s_t$.

At (9), a deep neural network $\Phi$ accepts $x_t$ and $s_{t-1}^r$ as inputs and outputs an updated estimated $s_t$. An example deep neural network suitable for completing the actions of (9) is shown and described in detail below in FIG. 4.

The Algorithm iterates actions (5) through (9) until $s_t$ converges or until a maximum number of iterations (e.g., three) is achieved, whichever occurs first. Thus, the Algorithm updates the estimated current retinal layer segmentation $s_t$ until it is suitable for use as a current retinal layer segmentation.

Figure 4:
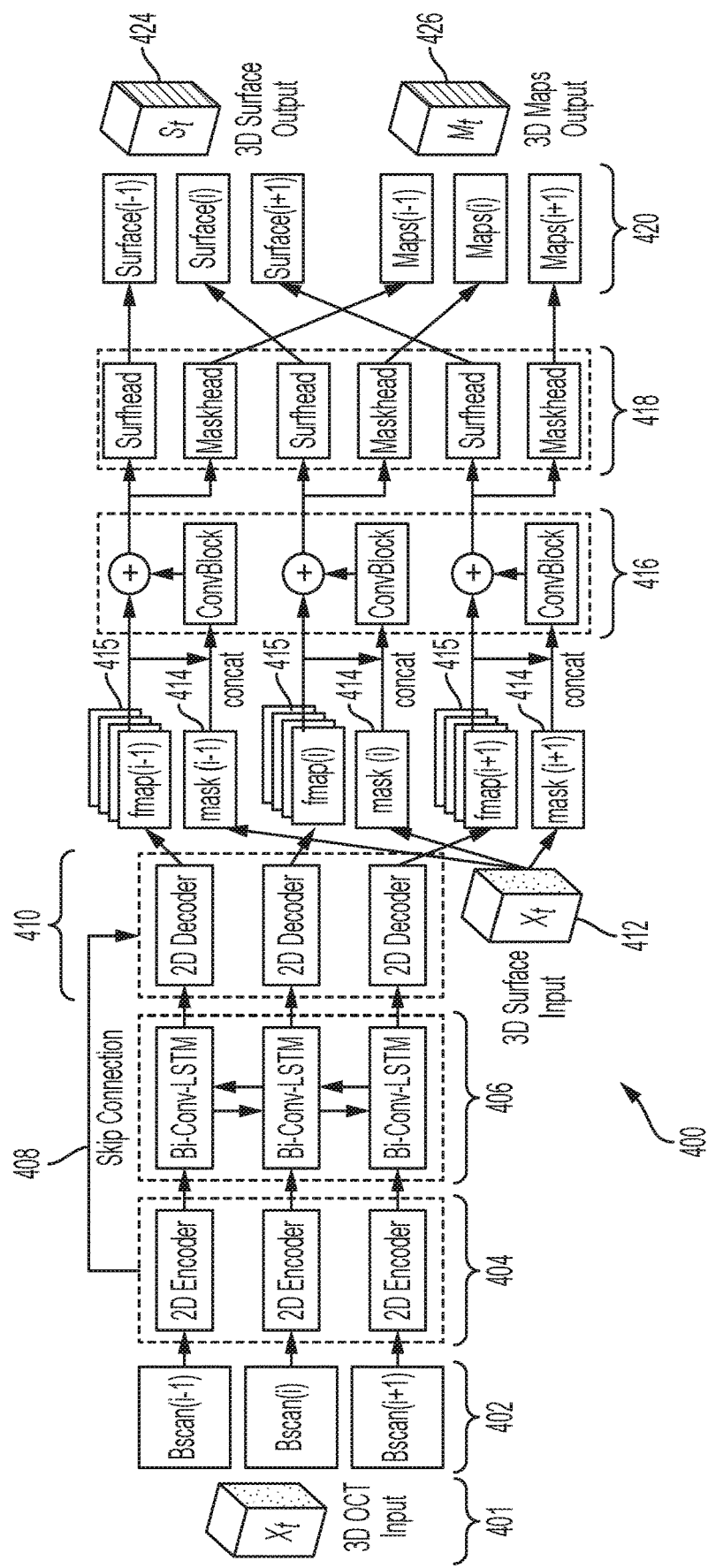
FIG. 4 is a schematic diagram of a deep neural network according to various embodiments.

FIG. 4 is a schematic diagram of a deep neural network 400 according to various embodiments. Neural network 400 may be implemented by computer 106 of FIG. 1 according to various embodiments. Due to memory constraints, some embodiments segment several adjacent B-scans 402 from volume $x_t$ 401 at a time, rather than segmenting the entire 3D OCT volume $x_t$ 401 in one forward pass through network 400.

2D encoders 404 extract features from the B-scans 402 individually, and the feature sequence from the 2D encoders 404 is sent into a bi-directional convolutional long-term-short-term memory networks 406. The output features for each B-scan now have inter-slice context. Those features are forwarded into 2D decoders 410 separately, which output feature maps 415 the same size as the input B-scans. There is a long skip connection 408 between the 2D encoders 404 and the 2D decoders 410.

The registered segmentation $s_{t-1}^r$ 412 from the previous visit represents the surface positions, which are converted into k channel binary layer masks 414 the same size as the input B-scans 401 (k is the total number of segmentation classes). The generated masks 414 are concatenated with the feature maps 415 and forwarded to convolutional networks 416. The output features from these convolutional networks 416 are considered as additional longitudinal information and added back to the previous feature maps 415 from the 2D decoders 410.

Now the feature maps 415 for each B-scan 402 have intra-slice, inter-slice, and longitudinal information, and are forwarded to two convolutional networks 418, Surfhead and Maskhead, which output current retinal layer segmentation $s_t$ 424 and layer maps $m_t$ 426. The layer $m_t$ may in practice be represented as an electronically stored 4D matrix of size [row number, column number, slice number], where each value is an integer c, (c=0, 1, 2, ..., N for N classes), such that $m_t[i, j, k]$ represents the class of voxel (i,j,k). The convolutional networks 418 include 3×3 convolution, batch normalization, and ReLU activation. The encoders of convolution networks 426 includes several 2×2 max pooling and convolutional networks. The decoders of convolutional networks 426 includs 2×2 nearest neighbor upsampling and convolution networks. An example embodiment of structure and training loss for network 400 is presented in He, Y., Carass, A., Yihao, L., Jedynak, B. M., Solomon, S. D., Saidha, S., Calabresi, P. A., and Prince, J. L., *Fully Convolutional Boundary Regression for Retina OCT Segmentation*, 22th International Conference on Medical Image Computing and Computer Assisted Intervention (MICCAI 2019), 2019, hereinafter, the "He et al. Paper".

Figure 5:
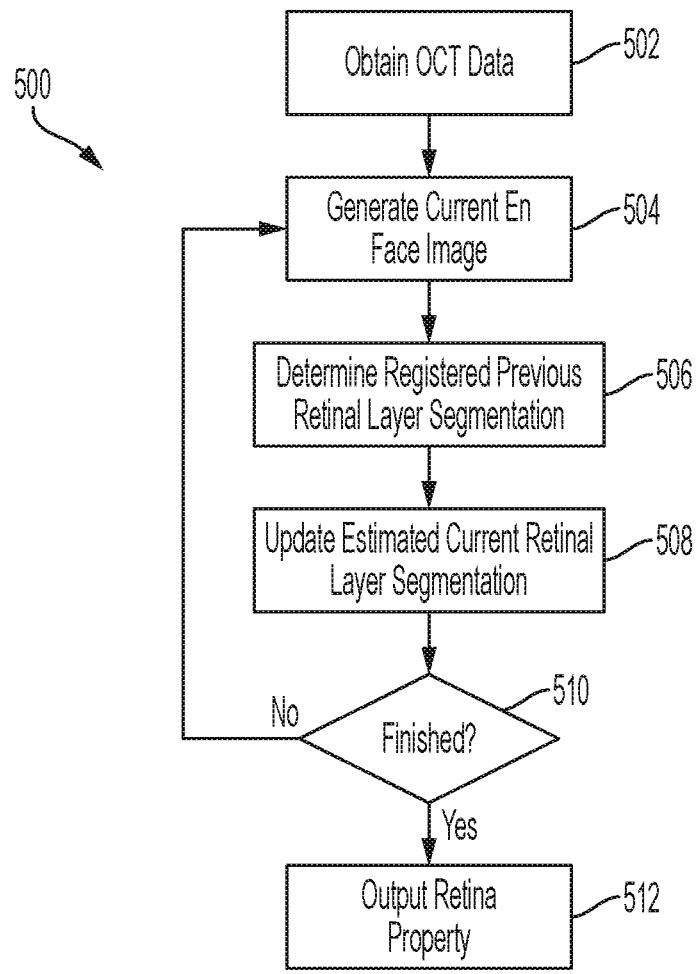
FIG. 5 is a flow diagram of a method of retinal layer segmentation according to various embodiments.

FIG. 5 is a flow diagram of a method 500 of retinal layer segmentation according to various embodiments. Method 500 may be implemented by a computer, e.g., computer 106 of FIG. 1, according to various embodiments.

At 502, method 500 obtains current OCT data, e.g., an OCT volume representing a retinal scan. Method 500 may obtain such data from OCT scanner 102 of FIG. 1 according to various embodiments.

At 504, method 500 generates a current en face image corresponding to the current OCT data and to an estimated current retinal layer segmentation. The actions of 504 may include some or all of action (3) as described above in reference to the Algorithm.

At 506, method 500 determines a registered previous retinal layer segmentation. The actions of 506 may include some or all of actions (5) through (8) as described above in reference to the Algorithm.

At 508, method 500 updates an estimated current retinal layer regimentation. The actions of 508 may include some or all of action (9) as described above in reference to the Algorithm.

At 510, method 500 determines whether to repeat 504, 506, and 508 by determining whether the estimated current retinal layer segmentation has converged, or whether a fixed number of iterations (e.g., three) has completed. If the estimated current retinal layer segmentation has not converged, and the fixed number of iterations has not completed, the control reverts to 504. Otherwise, control passes to 512.

At 512, method 500 outputs a property of the retina determined at least in part from the current retinal layer segmentation. The output property can be any of a variety of properties. For example, the output property may be a thickness of any retinal layer, e.g., total retina, outer plexiform layer, outer nuclear layer, inner segment, outer segment, retinal pigment epithelium, ganglion cell, inner plexiform layer, ganglion cell with inner plexiform layer, retinal nerve fiber, and inner nuclear layer. The output property may be the entire retinal layer segmentation, e.g., as represented by $s_t$ or layer map $m_t$, or may be a partial segmentation of any, or any combination, of layers. The output property may be an identification and location of a cyst, lesion, or other anomaly. Any output property may be determined from the current retinal layer segmentation provided by method 500 and confirmed by examining other related data, such as one or more current B-scans. Method 500 may conclude after 512.

Figure 6:
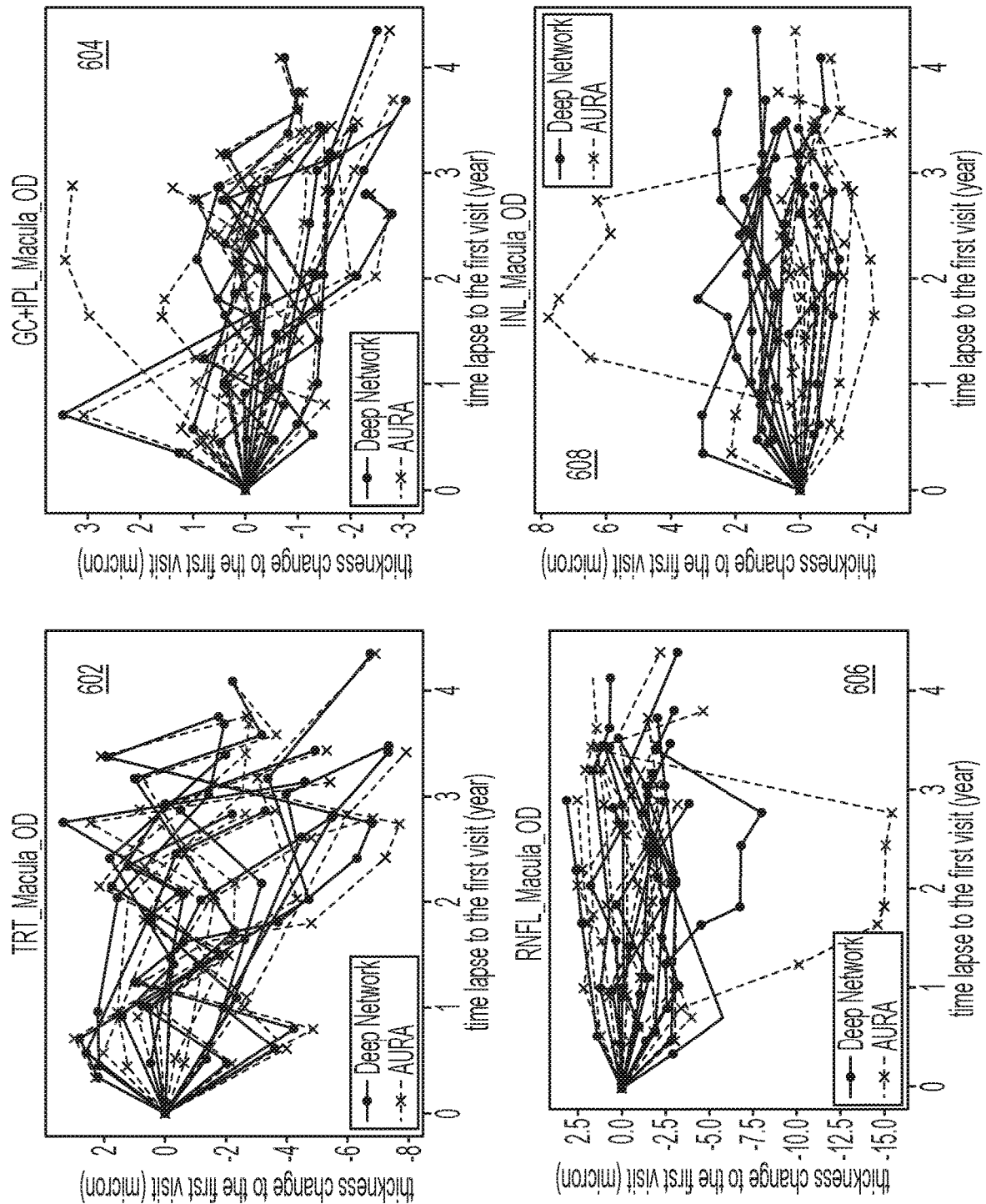
FIG. 6 depicts four graphs showing the trajectories of retinal thickness changes in several multiple sclerosis subjects and in healthy controls.

FIG. 6 depicts four graphs 602, 604, 606, 608 showing the trajectories of retinal thickness changes in several multiple sclerosis subjects and in healthy controls. The retinal thicknesses represented in the graphs were determined according to an embodiment and according to AURA, a state-of-the-art layer segmentation method. A dataset with 308 longitudinal standard-definition OCT scans from 71 subjects was used for training and validation. 257 scans of 59 subjects were used for training the neural network and the remainder were used as validation for early stopping of the training. The pseudo ground truth segmentation were generated with the AURA tool. The network was optimized with the default Adam optimizer and the loss function from the He et al. Paper, referenced above. Testing was done with two different cohorts, one comprising 68 longitudinal scans from 27 healthy controls and the other 75 longitudinal scans from 13 multiple sclerosis subjects. The age of all the subjects was between 18 and 100. The healthy controls had at least two longitudinal scans, and all the multiple sclerosis subjects had at least four longitudinal scans. The maximum iteration was set to three.

In FIG. 6, graph 602 depicts total retina thickness (TRT) at the macula. Graph 604 depicts ganglion cell and inner plexiform layer thickness (CG+IPL) at the macula. Graph 606 depicts retinal nerve fiber layer thickness (RNFL) at the macula. Graph 608 depicts inner nuclear layer thickness (INL) at the macula. As depicted, the example embodiment performs better than AURA.

The following Table depicts the root mean square error (RMSE) (in microns) linear fit of the multiple sclerosis subjects and the standard deviation (in microns) of the healthy controls evaluated by the embodiment (EM) of FIG. 6 and by AURA. The designations of layers are as above, with the additions of outer plexiform layer (OPL), outer nuclear layer (ONL), inner segment (IS), outer segment (OS), and retinal pigment epithelium (RPE). For the healthy controls, changes in the retinal thickness within a short period of time are not expected, so the Table depicts the standard deviation of the retinal thickness, where lower is better. For each multiple sclerosis subject, a linear model thickness=a×age+b is fit and the rooted mean square error (RMSE) is calculated. Note that the embodiment shows better consistency on total retinal thickness and numerous layers on both the multiple sclerosis subjects and healthy controls.

TABLE

|  | RNFL | GC + IPL | INL | OPL | ONL | IS | OS | RPE | TRT |
|---|---|---|---|---|---|---|---|---|---|
| Multiple Sclerosis RMSE Linear Fit | | | | | | | | | |
| AURA | 1.22 | 0.58 | 0.64 | 0.24 | 0.56 | 0.15 | 0.38 | 0.46 | 1.59 |
| EM | 0.92 | 0.52 | 0.47 | 0.13 | 0.59 | 0.17 | 0.23 | 0.51 | 1.51 |
| Healthy Controls | | | | | | | | | |
| AURA | 0.83 | 0.67 | 0.44 | 0.23 | 0.72 | 0.24 | 0.35 | 0.42 | 1.59 |
| EM | 0.72 | 0.83 | 0.64 | 0.20 | 0.73 | 0.22 | 0.27 | 0.53 | 1.41 |

In the Table, numbers in bold are preferable. As seen, the example embodiment is superior to AURA, which is considered a state-of-the-art technique.

Thus, embodiments may implement an iterative registration and segmentation technique for longitudinal retinal layer segmentation. Embodiments may avoid direct 3D OCT image interpolation of B-scans by surface interpolation and instead may transform and register the previous visit segmentation to the current visit, which is used as a segmentation prior. Embodiments may leverage the 3D context by aggregating features from a 2D network using convolutional long-short-term memory networks instead of just using 3D convolution. Thus embodiments may include a neural network that utilizes intra-slice, inter-slice, and longitudinal information for better and more consistent segmentation.

Certain embodiments can be performed using a computer program or set of programs. The computer programs can exist in a variety of forms both active and inactive. For example, the computer programs can exist as software program(s) comprised of program instructions in source code, object code, executable code or other formats; firmware program(s), or hardware description language (HDL) files. Any of the above can be embodied on a transitory or non-transitory computer readable medium, which include storage devices and signals, in compressed or uncompressed form. Exemplary computer readable storage devices include conventional computer system RAM (random access memory), ROM (read-only memory), EPROM (erasable, programmable ROM), EEPROM (electrically erasable, programmable ROM), and magnetic or optical disks or tapes.

While the invention has been described with reference to the exemplary embodiments thereof, those skilled in the art will be able to make various modifications to the described embodiments without departing from the true spirit and scope. The terms and descriptions used herein are set forth by way of illustration only and are not meant as limitations. In particular, although the method has been described by examples, the steps of the method can be performed in a different order than illustrated or simultaneously. Those skilled in the art will recognize that these and other variations are possible within the spirit and scope as defined in the following claims and their equivalents.

What is claimed is:

1. A method of retinal layer segmentation, the method comprising:
   obtaining current optical coherence tomography (OCT) data for a retina;
   generating an estimated current en face image based on the current OCT data and an estimated current retinal layer segmentation;
   determining a registered previous retinal layer segmentation based on a previous retinal layer segmentation, a previous en face image, the estimated current en face image, and the estimated current retinal layer segmentation;
   updating the estimated current retinal layer segmentation using a deep neural network and based on the current OCT data and the registered previous retinal layer segmentation;
   repeating the generating, the determining, and the updating to obtain a current retinal layer segmentation as the estimated current retinal layer segmentation, wherein the repeating comprises repeating until either a predetermined number of repetitions is completed or until the estimated current retinal layer segmentation converges; and
   outputting a property of the retina determined at least in part from the current retinal layer segmentation.

2. The method of claim 1, wherein the property of the retina comprises a thickness of the retina.

3. The method of claim 1, wherein the property of the retina comprises the current retinal layer segmentation.

4. The method of claim 1, wherein the determining the registered previous retinal layer segmentation comprises:
   obtaining a transformation that registers the previous en face image to the estimated current en face image;
   applying the transformation to the previous retinal layer segmentation to align the previous retinal layer segmentation with the estimated current retinal layer segmentation in an en face plane, wherein a transformed previous retinal layer segmentation is obtained; and
   shifting the transformed previous retinal layer segmentation axially to align with a predetermined retinal layer, wherein the registered previous retinal layer segmentation is obtained.

5. The method of claim 1, further comprising outputting a current three-dimensional retinal layer map.

6. The method of claim 1,
wherein the current OCT data comprises a plurality of two-dimensional images;
wherein the deep neural network comprises a plurality of two-dimensional encoders and a plurality of convolutional long-short-term memory networks; and
wherein the updating the estimated current retinal layer segmentation using the deep neural network comprises:
extracting, using the plurality of two-dimensional encoders, intra-slice features from the two-dimensional scans; and
extracting, using the plurality of convolutional long-short-term memory networks and based on the intra-slice features, inter-slice features from the two-dimensional scans.

7. The method of claim 1,
wherein the deep neural network comprises a plurality of convolutional networks; and
wherein the updating the estimated current retinal layer segmentation using the deep neural network comprises generating, by the plurality of convolutional networks, longitudinal priors for retinal layers based on at least the registered previous retinal layer segmentation.

8. The method of claim 1, further comprising assessing a progression of multiple sclerosis based on the property of the retina.

9. The method of claim 1, wherein the current retinal layer segmentation comprises at least three retinal layers.

10. A system for retinal layer segmentation, the system comprising at least one electronic processor and non-transitory computer readable instructions that configure the at least one processor to perform operations comprising:
obtaining current optical coherence tomography (OCT) data for a retina;
generating an estimated current en face image based on the current OCT data and an estimated current retinal layer segmentation;
determining a registered previous retinal layer segmentation based on a previous retinal layer segmentation, a previous en face image, the estimated current en face image, and the estimated current retinal layer segmentation;
updating the estimated current retinal layer segmentation using a deep neural network and based on the current OCT data and the registered previous retinal layer segmentation;
repeating the generating, the determining, and the updating to obtain a current retinal layer segmentation as the estimated current retinal layer segmentation, wherein the repeating comprises repeating until either a predetermined number of repetitions is completed or until the estimated current retinal layer segmentation converges; and
outputting a property of the retina determined at least in part from the current retinal layer segmentation.

11. The system of claim 10, wherein the property of the retina comprises a thickness of the retina.

12. The system of claim 10, wherein the property of the retina comprises the current retinal layer segmentation.

13. The system of claim 10, wherein the determining the registered previous retinal layer segmentation comprises:
obtaining a transformation that registers the previous en face image to the estimated current en face image;
applying the transformation to the previous retinal layer segmentation to align the previous retinal layer segmentation with the estimated current retinal layer segmentation in an en face plane, wherein a transformed previous retinal layer segmentation is obtained; and
shifting the transformed previous retinal layer segmentation axially to align with a predetermined retinal layer, wherein the registered previous retinal layer segmentation is obtained.

14. The system of claim 10, wherein the operations further comprise outputting a current three-dimensional retinal layer map.

15. The system of claim 10,
wherein the current OCT data comprises a plurality of two-dimensional images;
wherein the deep neural network comprises a plurality of two-dimensional encoders and a plurality of convolutional long-short-term memory networks; and
wherein the updating the estimated current retinal layer segmentation using the deep neural network comprises:
extracting, using the plurality of two-dimensional encoders, intra-slice features from the two-dimensional scans; and
extracting, using the plurality of convolutional long-short-term memory networks and based on the intra-slice features, inter-slice features from the two-dimensional scans.

16. The system of claim 10,
wherein the deep neural network comprises a plurality of convolutional networks; and
wherein the updating the estimated current retinal layer segmentation using the deep neural network comprises generating, by the plurality of convolutional networks, longitudinal priors for retinal layers based on at least the registered previous retinal layer segmentation.

17. The system of claim 10, wherein the operations further comprise assessing a progression of multiple sclerosis based on the property of the retina.

18. The system of claim 10, wherein the current retinal layer segmentation comprises at least three retinal layers.

19. A method of retinal layer segmentation, the method comprising:
obtaining current optical coherence tomography (OCT) data for a retina;
generating an estimated current en face image based on the current OCT data and an estimated current retinal layer segmentation;
determining a registered previous retinal layer segmentation based on a previous retinal layer segmentation, a previous en face image, the estimated current en face image, and the estimated current retinal layer segmentation;
updating the estimated current retinal layer segmentation using a deep neural network and based on the current OCT data and the registered previous retinal layer segmentation;
repeating the generating, the determining, and the updating to obtain a current retinal layer segmentation as the estimated current retinal layer segmentation;
outputting a property of the retina determined at least in part from the current retinal layer segmentation; and
assessing a progression of multiple sclerosis based on the property of the retina.

20. A system for retinal layer segmentation, the system comprising at least one electronic processor and non-transitory computer readable instructions that configure the at least one processor to perform operations comprising:
obtaining current optical coherence tomography (OCT) data for a retina;

generating an estimated current en face image based on the current OCT data and an estimated current retinal layer segmentation;

determining a registered previous retinal layer segmentation based on a previous retinal layer segmentation, a previous en face image, the estimated current en face image, and the estimated current retinal layer segmentation;

updating the estimated current retinal layer segmentation using a deep neural network and based on the current OCT data and the registered previous retinal layer segmentation;

repeating the generating, the determining, and the updating to obtain a current retinal layer segmentation as the estimated current retinal layer segmentation;

outputting a property of the retina determined at least in part from the current retinal layer segmentation; and assessing a progression of multiple sclerosis based on the property of the retina.

* * * * *